United States Patent [19]

Takamura et al.

[11] Patent Number: 5,183,045
[45] Date of Patent: Feb. 2, 1993

[54] NMR MEASURING METHOD AND MEASURING APPARATUS FOR TISSUE OF A LIVING BODY

[75] Inventors: Susumu Takamura, Kusatsu; Takashi Nakamura; Makoto Okawauchi, both of Shiga; Harumi Toda, Kyoto; Ichiro Kanki, Hirakata; Minoru Yoshida, Shiga; Toshiyuki Imoto, Kyoto; Naomi Negayama, Amagasaki; Koichi Oka, Kusatsu, all of Japan

[73] Assignee: Otsuka Electronic Co., Ltd., Osaka, Japan

[21] Appl. No.: 460,336

[22] PCT Filed: Jun. 12, 1989

[86] PCT No.: PCT/JP89/00589
§ 371 Date: Apr. 16, 1990
§ 102(e) Date: Apr. 16, 1990

[87] PCT Pub. No.: WO89/12422
PCT Pub. Date: Dec. 28, 1989

[30] Foreign Application Priority Data
Jun. 17, 1988 [JP] Japan ................. 63-150899

[51] Int. Cl.⁵ .............................. A61B 5/055
[52] U.S. Cl. .............. 128/653.2; 128/653.5; 324/309; 324/318; 436/173
[58] Field of Search ............ 128/653.2, 653.5; 324/300, 307, 309, 318, 321; 436/173

[56] References Cited

U.S. PATENT DOCUMENTS

| | | | |
|---|---|---|---|
| 4,291,271 | 9/1981 | Lauffer | 324/307 |
| 4,409,550 | 10/1983 | Fossel et al. | 324/300 |
| 4,413,233 | 11/1983 | Fossel et al. | 324/300 |
| 4,607,226 | 8/1986 | Zeiger | 324/318 |
| 4,639,364 | 1/1987 | Hoey | 128/653.2 |
| 4,642,569 | 2/1987 | Hayes et al. | 324/318 |
| 4,775,836 | 10/1988 | Starewicz et al. | 324/318 |
| 4,998,065 | 3/1991 | Koizumi | 324/318 |
| 5,072,732 | 12/1991 | Rapoport et al. | 128/653.2 |

*Primary Examiner*—Lee S. Cohen
*Assistant Examiner*—Krista M. Pfaffle
*Attorney, Agent, or Firm*—Sughrue, Mion, Zinn, Macpeak & Seas

[57] ABSTRACT

There is carried out an NMR measurement in which a receiver coil (7) for receiving an NMR free induction signal comes in contact with or in close vicinity to one side of tissue of a living body (1) immersed in a perfusion solution (4), while a portion or whole body of the receiver coil (7) is so held as not to come in contact with the perfusion solution (4). According to this measuring method, since a portion or whole body of the receiver coil (7) does not come in contact with the perfusion solution (4), the receiver coil (7) is hardly subject to the electromagnetic influence of changes in the perfusion solution (4). This prevents the free induction signal from being embedded in noise, assuring measurement with high sensitivity. Even for a large-size internal organ, only a signal from an area presenting a uniform magnetic field may be acquired, since the measurement is carried out with the receiver coil (7) coming in contact with or in close vicinity to one side of the internal organ. Thus, a high-resolution free induction signal may be acquired.

12 Claims, 6 Drawing Sheets

RECEIVER COIL
7

RESIN
6a 7
6a

NMR MEASURING METHOD AND MEASURING APPARATUS FOR TISSUE OF A LIVING BODY

FIELD OF THE INVENTION

The present invention relates to NMR measuring method and apparatus thereof for tissue of a living body, in which the measurement is carried out while changing the concentration of a perfusion solution.

BACKGROUND OF THE INVENTION

Nuclear magnetic resonance absorption has been conventionally used as means for analyzing chemical substances and clarifying reaction processes. In recent years, nuclear magnetic resonance absorption has become the object of public attention in a variety of medical fields through NMR zeugmatography or the like for observing the distribution of components of tissue of a living body.

For example, it is common practice in order to make clear transplant adaptability of an internal organ, energy metabolism or the like, to conduct an NMR measurement test on an internal organ, a muscle or the like of an experimental animal under cultivation in a perfusion solution. More specifically, an internal organ of a living thing disposed in a perfusion cell is placed in a static magnetic field, and a free decay signal (free induction signal) obtained by applying a rotating magnetic field in the form of a pulse is measured by a receiver coil disposed around the cell. The free induction signal is analyzed to obtain an NMR spectrum. Based on the NMR spectrum thus obtained, it is possible to clarify the condition of phosphorus atoms contained in phosphorus compounds such as creatinic acid, ATP, inorganic phosphoric acid and the like. Thus, the transplant adaptability of the internal organ may be judged.

FIG. 9 shows the arrangement of a conventional measuring apparatus. In FIG. 9, an internal organ or the like of a small animal is put in a cell 22 around which a receiver coil 21 is wound and which is perfused with a perfusion solution (a physiological saline solution or the like). With a static magnetic field H applied to the receiver coil 21 at a right angle to the axis thereof, a free induction signal generated in the receiver coil 21 is detected.

According to this apparatus, an NMR measurement may be carried out for a long period of time while the perfusion solution prevents the internal organ or muscle from being dried.

However, when the concentration of the perfusion solution is changed with the passage of time and the corresponding changes in the absorption spectrum with the passage of time are to be analyzed, the above-mentioned arrangement presents the following problem.

The perfusion solution flows in the receiver coil. Accordingly, when carrying out a measurement with a changing concentration of the perfusion solution the inductance of the receiver coil is changed according to the changes in concentration of the perfusion solution. This assures neither tuning of, the receiver coil, nor matching of the impedance and not only changes the appearing position of the absorption spectrum, but also weakens the absorption spectral line, causing this line to be embedded in noise. Thus, no accurate measurement may be carried out.

In this connection, perfusion solutions having different concentrations are conventionally prepared, and each time each perfusion solution flows, the tuning of the receiver coil is done over again and measurement is then carried out. This not only makes the measurement troublesome, but also fails to acquire the data corresponding to continuous changes in concentration.

Further, in the above-mentioned arrangement, even though the cell is made in a large size and a large-size internal organ is housed therein, the current art may provide only a small area presenting a uniform static magnetic field. This causes the internal organ to partially protrude from the uniform magnetic field, thereby to disadvantageously deteriorate the resolution of an NMR spectral signal obtained by analyzing the free induction signal.

It is an object of the present invention to provide NMR measuring method and apparatus for tissue of a living body, capable of acquiring a highly sensitive measurement signal even though the measurement is made with concentration of a perfusion solution and capable of also measuring also a large-size internal organ.

DISCLOSURE OF THE INVENTION

To achieve the above-mentioned object, the inventor does not adopt the conventional arrangement that an internal organ is placed inside of a receiver coil for receiving an NMR free induction signal. To cope with the need to measure a large-size internal organ and to minimize the influence of a perfusion solution exerted upon the electric nature of the receiver coil, the inventor has tried to measure a signal from the internal organ without the receiver coil coming in contact with the perfusion solution. In this connection, the inventor adopts a method of carrying out an NMR measurement with a receiver coil for receiving an NMR free induction signal coming in contact with or in close vicinity to one side of tissue of a living body immersed in a perfusion solution, while a part or whole body of the receiver coil is so held as not to come in contact with the perfusion solution.

According to the above-mentioned measuring method the measurement is carried out with the receiver coil coming in contact with or in close vicinity to tissue of a living body immersed in the perfusion solution while the concentration of the perfusion solution is being changed. Since a part or whole body of the receiver coil does not come in contact with the perfusion solution, the receiver coil is hardly subject to the electromagnetic influence of the changes in concentration of the perfusion solution. This prevents the free induction signal from being embedded in noise. Thus, the measurement may be carried out with good sensitivity.

Even for a large-size internal organ, it is possible to acquire only a signal from the area presenting a uniform magnetic field, since the measurement is carried out with the receiver coil coming in contact with or in close vicinity to one surface of the internal organ. Accordingly, a free induction signal having high resolution may be acquired.

According to the present invention, the NMR measuring apparatus for tissue of a living body has a receiver coil for receiving an NMR free induction signal from one side of the living body tissue, and a portion or all of the coil is surrounded by material which does not exert a negative influence upon transmission of the free induction signal, such that the coil does not come in contact with the perfusion solution.

According to this apparatus, a portion or whole body of the above-mentioned coil is surrounded by the material enabling it to prevent the entry of the perfusion solution in the coil. Thus, an accurate measurement may be carried out without change in the electric characteristics of the receiver coil.

BRIEF DESCRIPTION OF THE DRAWINGS

FIG. 1 (b) is a section view in side elevation of the apparatus in FIG. 1 (a);

PREFERRED EMBODIMENT OF THE INVENTION

Figure 1A:
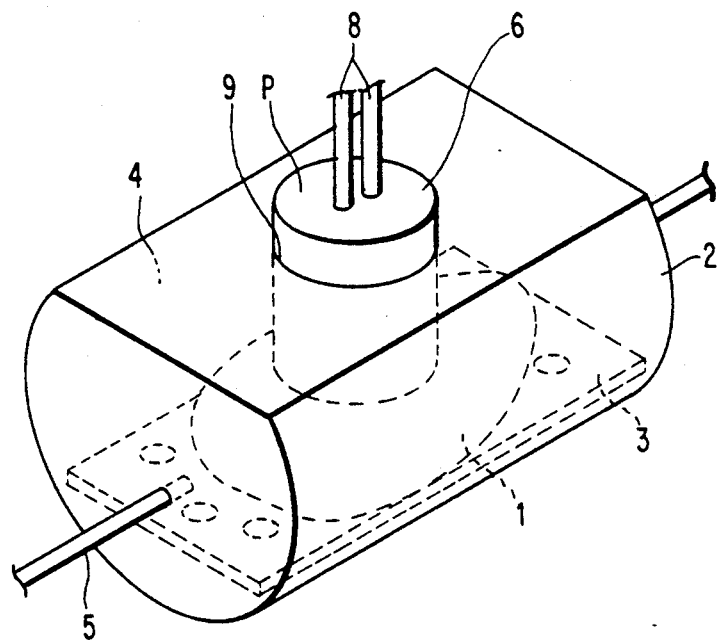
FIG. 1 (a) is a perspective view of an NMR measuring apparatus for tissue of a living body in accordance with an embodiment of the present invention.

The following description will discuss embodiments of the present invention with reference to the attached drawings.

FIG. 1 (a) is a perspective view illustrating the arrangement of NMR measuring apparatus for tissue of a living body.

A perfusion cell 2 is perfused with a perfusion solution (for example, a phosphoric acid solution, a physiological saline solution) 4. The perfusion solution 4 flows into the perfusion cell 2 by introducing the perfusion solution 4 contained in a perfusion solution tank (not shown), through a perfusion pipe 5. The perfusion cell 2 is vertically divided by a receiving plate 3 having a plurality of holes through which the perfusion solution 4 passes. Tissue of a living body (for example, an internal organ of an animal) 1 is placed on the receiving plate 3.

A receiver coil 7 for receiving an NMR free induction signal is housed in a cylindrical container 6 made of Juracon resin, polytetrafluorinated ethylene resin, acrylic resin or the like such that the perfusion solution 4 does not enter into the container 6 (See FIG. 1 (b)). The Juracon resin, polytetrafluorinated ethylene resin, acrylic resin and the like are selected because they exert no adverse effect on the transmission of the free induction signal. The container 6 is filled with air. Lead lines 8 are lead from the receiver coil 7 and connected to the NMR measuring apparatus 10. The container 6 is inserted, through an O-ring 11, into an insertion hole 9 on the top surface of the perfusion cell 2 such that the bottom of the container 6 may come in contact with the internal organ 1. In the following description, the receiver coil 7 and the container 6 are generally referred to as a probe P. A static magnetic field H forms a uniform magnetic field at least under the receiver coil 7.

With the internal organ 1 housed in the perfusion cell 2 which is perfused with the perfusion solution 4, the probe P is inserted into the insertion hole 9 so that the bottom of the probe P comes in contact with the top surface of the internal organ 1. This enables the receiver coil 7 to detect a free induction signal of the internal organ 1. At this time, the receiver coil 7 may be so held as not to come in contact with the perfusion solution 4 since the perfusion solution 4 does not enter into the container 6. Further, since the bottom of the probe P comes in contact with the internal organ 1, i.e., since the perfusion solution 4 is not present between the receiver coil 7 and the internal organ 1, the electric characteristics of the receiver coil 7 are hardly subject to the direct influence of changes in the concentration of the perfusion solution 4, if any. Thus, the receiver coil 7 may receive an accurate and highly sensitive signal.

Figure 2:
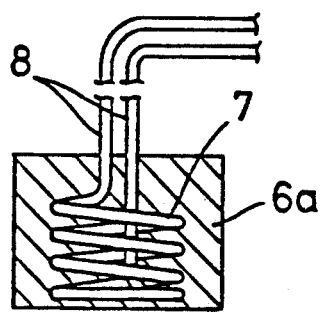
FIG. 2 is a view of a receiver coil molded with resin.
Figure 3:
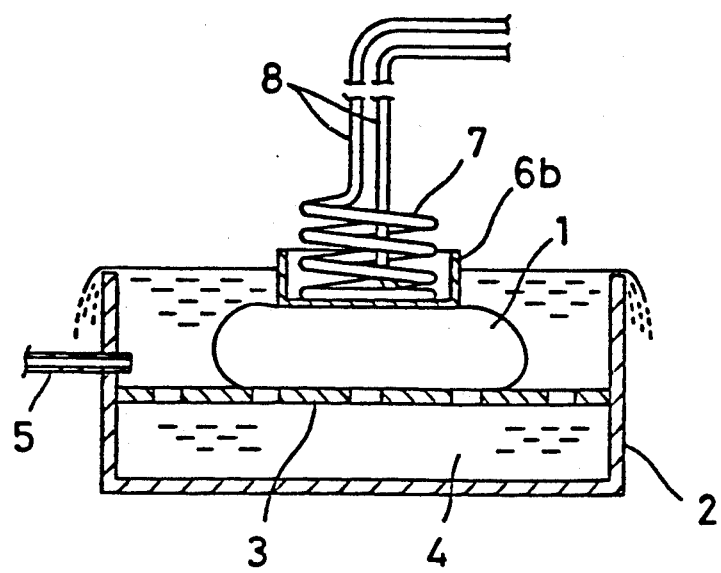
FIG. 3 is a view of an example of the present invention in which only a portion of the receiver coil is surrounded by a container.
Figure 10A:
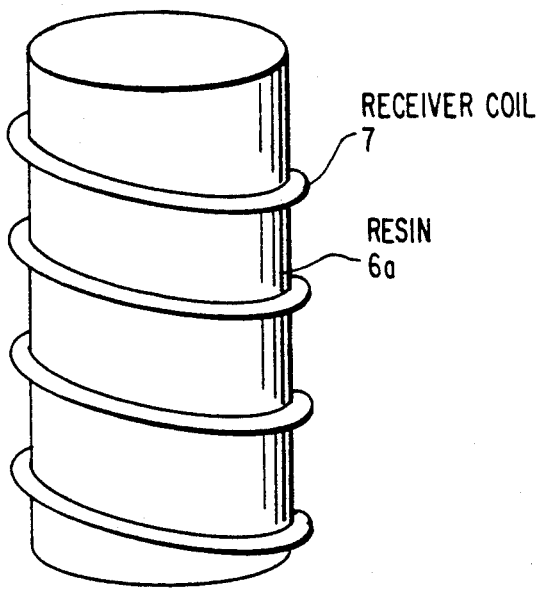
FIG. 10 is a view of a receiver coil having resin therein.
Figure 10B:
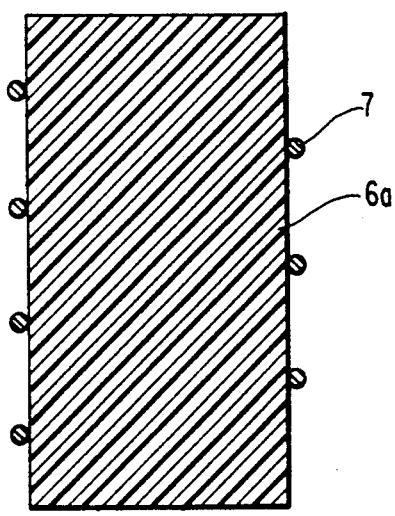

According to the present invention, the probe P may be formed only by a receiver coil 7 which is molded with resin 6a or filled at the periphery and/or inside thereof with the resin 6a, as shown in FIG. 2. In addition, the receiver coil may be filled inside thereof with the resin, as shown in FIG. 10. Alternatively, there may be used a cylindrical container 6b which surrounds only a portion of a receiver coil 7, as shown in FIG. 3.

Figure 1B:
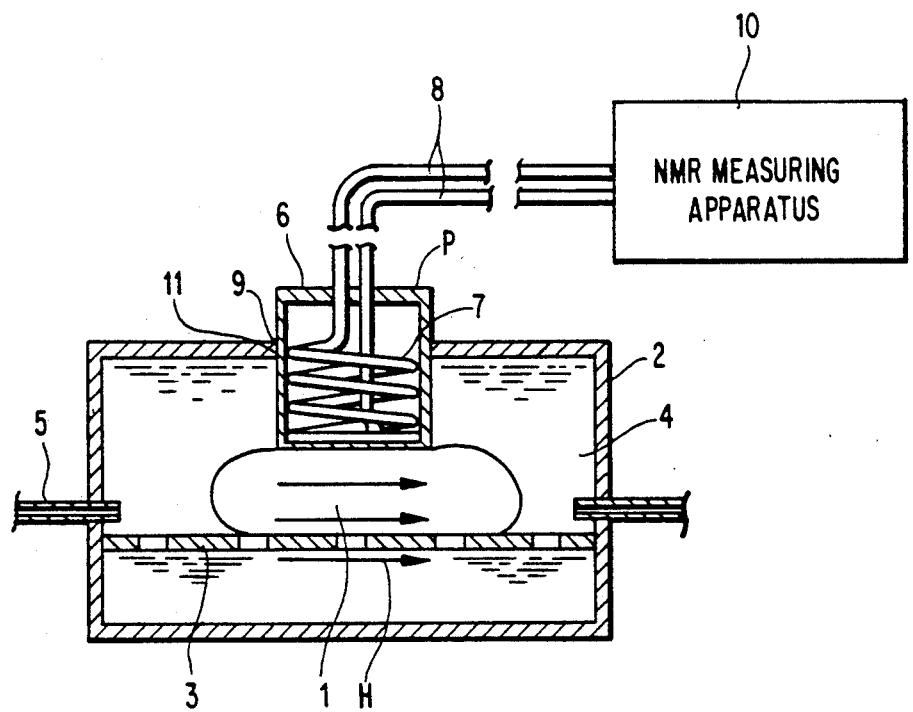
Figure 4:
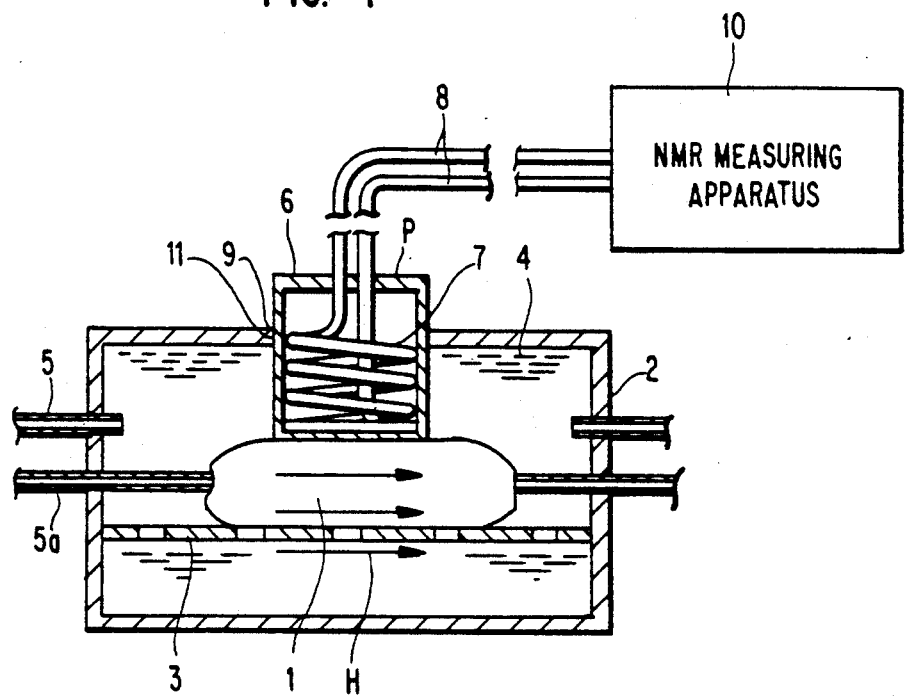
FIG. 4 is a section view in side elevation of the NMR measuring apparatus for tissue of a living body in accordance with another embodiment of the present invention.

In the embodiment of FIGS 1(a) and 1(b), the measurement is carried out while the internal organ 1 is immersed in the perfusion solution 4. However, the measurement may also be carried out while the internal organ 1 is immersed in the perfusion solution 4 and a medical agent is injected into a blood vessel or the like of the internal organ 1. FIG. 4 shows such an arrangement. In the embodiment in FIG. 4, a medical agent injecting pipe 5a is disposed and connected to a blood vessel or the like of the internal organ 1. According to this arrangement, it is possible to measure changes in an NMR signal which result from the injection of the medical agent, or changes in an NMR signal which result from changes in the concentration of the medical agent.

Figure 5:
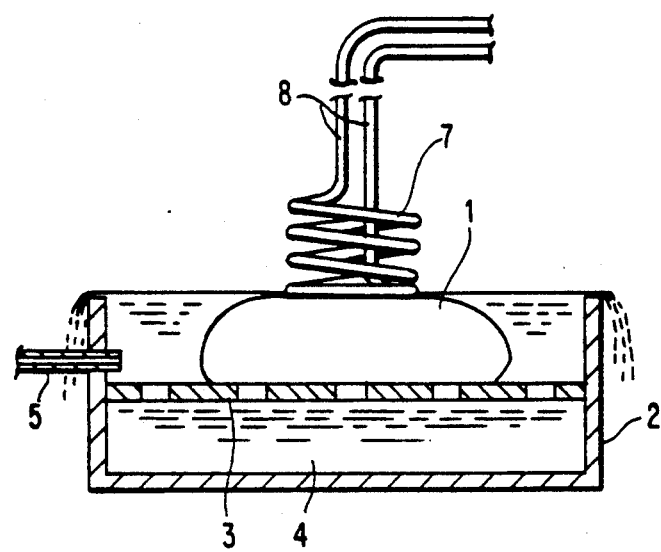
FIGS. 5 to 7 are views illustrating portions of another apparatus for carrying out an NMR measuring method for tissue of a living body.

FIG. 5 shows the arrangement of another measuring apparatus embodying an NMR measuring method in accordance with the present invention. According to this arrangement, a perfusion cell 2 is opened at the upper portion thereof so that a perfusion solution 4 contained in the perfusion cell 2 overflows from the opening of the cell 2. An internal organ 1 is placed on a receiving plate 3 in the perfusion cell 2. The level of the receiving plate 3 is adjusted such that the upper surface of the internal organ 1 is located immediately under the level of the perfusion solution 4. With such an arrangement, a coil 7 directly comes in contact with the internal organ 1. Only that surface of the receiver coil 7 which comes in contact with the internal organ 1, is contacted with the perfusion solution 4, and the receiver coil 7 may receive a signal without the coil 7 being immersed with the perfusion solution 4. Thus, an accurate NMR measurement may be achieved.

Figure 6:
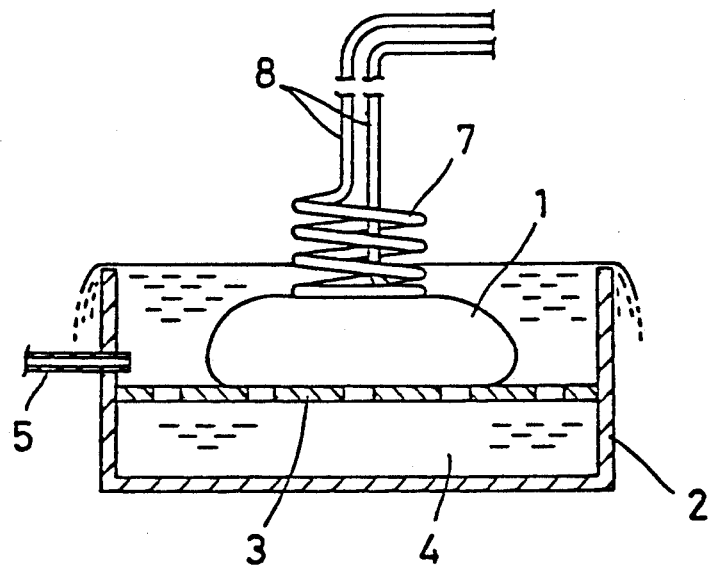

Measurement may also be carried out with a portion of the receiver coil 7 immersed in the perfusion solution 4 as shown in FIG. 6, instead of the arrangement shown in FIG. 5. According to the arrangement in FIG. 6, the receiver coil 7 may receive a signal without a major portion of the receiver coil 7 being immersed with the perfusion solution 4. Thus, a good signal may be received.

Figure 7:
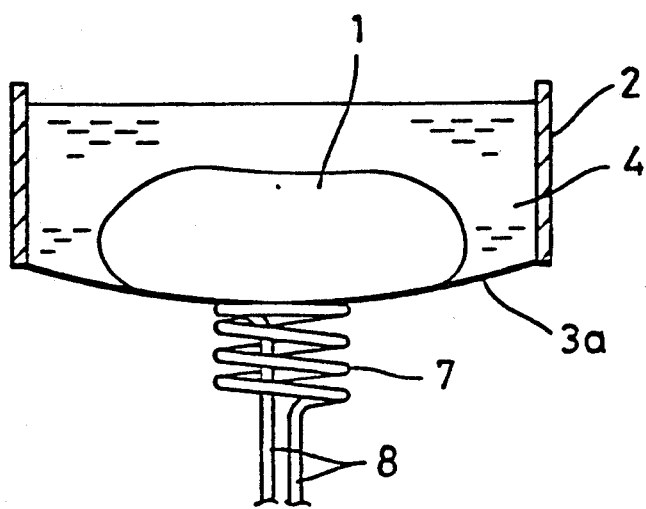

FIG. 7 shows the arrangement of a further measuring apparatus for embodying the NMR measuring method. In FIG. 7, a thin film 3a is attached to the bottom of a perfusion cell 2. The perfusion cell 2 is perfused with a perfusion solution 4, and an internal organ 1 is placed on this film 3a. Under the film 3a, a coil 7 comes in contact with the film 3a so that a signal is received by the receiver coil 7. Likewise in the arrangements above-mentioned, the receiver coil 7 may receive a signal without the coil 7 coming in contact with the perfusion solution 4. Thus, an accurate NMR measurement may be carried out.

According to the present invention, the measurement may also be carried out while a low-temperature perfusion solution flows to hold the temperature of the internal organ at a low temperature.

The present invention should not be limited to the embodiments above-mentioned. For example, in the embodiment in FIG. 1(a), 1(b), 3, 4 or 6, the measurement may be carried out with the probe being slightly separated from the living body. In this case, a slight amount of the perfusion solution is present between the receiver coil and the tissue of the living body. Still, a fairly accurate signal may be acquired. Although the receiver coil is wound in the form of a solenoid in the embodiments above-mentioned, the receiver coil maybe, for example, a single-fold coil. Further a variety of modifications of the present invention may be made without departing from the scope of the invention.

EXAMPLE

Figure 8:
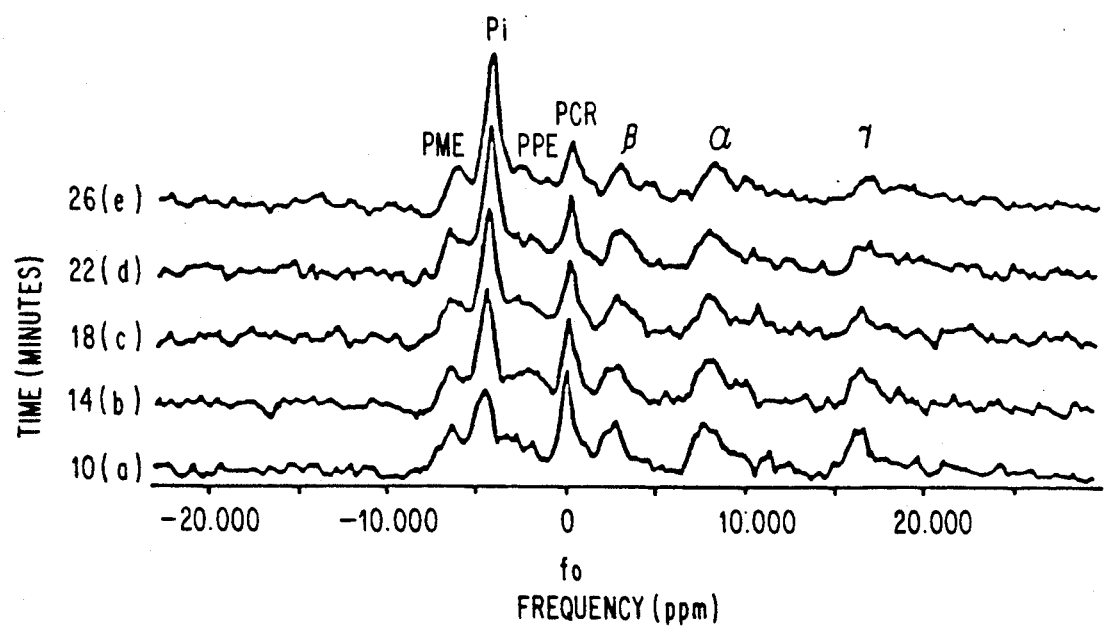
FIG. 8 is a graph illustrating measured data of NMR spectra.
Figure 9:
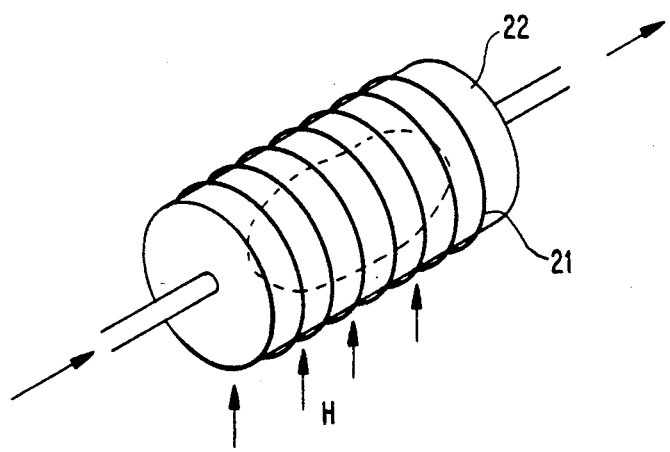
FIG. 9 is a perspective view of a conventional NMR measuring apparatus for tissue of a living body.

An NMR measurement was carried out with the use of the NMR measuring apparatus shown in FIGS. 1(a) and 1(b) and a mixture solution of a physiological saline solution with propionic acid, as the perfusion solution. As the tissue of a living body, the brain of a rat was used. The concentration of the propionic acid in the physiological saline solution was initially set to 10 millimols. A 100-millimol propionic acid solution was gradually added to the mixture solution so that the concentration of the propionic acid flowing in the perfusion cell 2 was changed from 10 millimols to 100 millimols. Under the conditions above-mentioned, the spectra of phosphorus were measured. FIG. 8 shows the results of such a measurement. In FIG. 8, curves (a) to (e) respectively show spectra measured after 10 minutes, 14 minutes, 18 minutes, 22 minutes and 26 minutes which passed after the addition of the 100-millimol solution had started.

As apparent from FIG. 8, the spectral waveforms are not shifted even with changes in the concentration of the propionic acid, and the peak height undergoes a change with the concentration. Thus, it is made sure that an accurate NMR measurement was carried out.

According to the NMR measuring method for tissue of a living body of the present invention, measurement is carried out without at least a portion of the receiver coil coming in contact with the perfusion solution. This may reduce the influence of potential changes in the concentration of the perfusion solution exerted upon the electric characteristics of the receiver coil. Accordingly, an accurate and highly sensitive signal may be acquired. Further, the measurement is carried out with the coil coming in contact with or in close vicinity to one side of tissue of a living body. Accordingly, even for large-size tissue, only a signal from an area presenting a uniform magnetic field may be acquired. Thus, there may be measured, with good precision, the reaction of tissue of a living body including large-size tissue, with respect to changes in the concentration of the perfusion solution.

According to the NMR measuring apparatus for tissue of a living body of the present invention, a signal may be measured without the receiver coil for receiving an NMR induction signal coming in contact with the perfusion solution. Thus, the NMR measuring method for tissue of a living body above-mentioned may be readily embodied with the use of the apparatus.

We claim:
1. An NMR measuring method for tissue of a living body immersed in a perfusion solution comprising
  (1) immersing the tissue of the living body in the perfusion solution,
  (2) placing a receiver coil for receiving an NMR free induction signal in contact with or in close vicinity to only one side of the tissue,
  (3) holding the receiver coil to prevent contact with the perfusion solution, and
  (4) obtaining an NMR measurement.
2. An NMR measuring method for tissue of a living body immersed in a perfusion solution comprising
  (1immersing the tissue of the living body in the perfusion solution,
  (2placing a receiver coil for receiving an NMR free induction signal in contact with or in close vicinity to only one side of the tissue,
  (3) holding the receiver coil so that only a part of the receiver coil comes in contact with the perfusion solution, and
  (4) obtaining an NMR measuring.
3. An NMR measuring apparatus for tissue of a living body immersed in a perfusion solution comprising
  a perfusion cell which receives a perfusion solution,
  a means for generating an NMR free induction signal,
  a receiver coil for receiving the NMR free induction signal connection to said means for generating an NMR free induction signal.
  a material, which does not exert a negative influence upon a transmission of the free induction signal, partially or completely surrounding the receiver coil,
  a measuring device coupled to the receiver coil,
  wherein the receiver coil does not come into contact with the perfusion solution, and the receiver coil is placed in contact with or in close vicinity to only one side of the tissue of the living body.
4. An NMR measuring apparatus for tissue of a living body as set forth in claim 3, wherein the material forms a container which completely surrounds the receiver coil.
5. An NMR measuring apparatus for tissue of a living body as set forth in claim 3, wherein the material forms a container which partially surrounds the receiver coil.
6. An NMR measuring apparatus for tissue of a living body as set forth in claim 3, wherein the inside of the receiver coil is filled with a resin.
7. An NMR measuring apparatus for tissue of a living body as set forth in claim 3, wherein the material is a container made of a resin selected from the group consisting of Juracon resin, polytetrafluorinated ethylene resin, and acrylic resin.
8. An NMR measuring apparatus for tissue of a living body as set forth in claim 3, wherein the material is a resin.
9. An NMR measuring apparatus for tissue of a living body as set forth in claim 3, wherein the receiver coil is molded with a resin.
10. An NMR measuring apparatus for tissue of a living body as set forth in claim 3, wherein the perfusion solution is selected from the group consisting of phosphoric acid and physiological saline solution.

11. An NMR measuring method for tissue of a living body immersed in a perfusion solution or by a flowing perfusion solution comprising:
  (1) immersing the tissue of the living body in the perfusion solution or by the flowing perfusion solution and changing the concentration of the perfusion solution or the flowing perfusion solution over time,
  (2) placing a receiver coil for receiving an NMR free induction signal in contact with or in close vicinity to only one side of the tissue,
  (3) holding the receiver coil to prevent contact with the perfusion solution or the flowing perfusion, and
  (4) obtaining an NMR measurement.

12. An NMR measuring method for tissue of a living body immersed in a perfusion solution or by a flowing perfusion solution comprising:
  (1) immersing the tissue of the living body in the perfusion solution or by the flowing perfusion solution and changing the concentration of the perfusion solution or the flowing perfusion solution over time;
  (2) placing a receiver coil for receiving an NMR free induction signal in contact with or in close vicinity to only one side of the tissue,
  (3) holding the receiver coil so that only a part of the receiver coil comes in contact with the perfusion solution or the flowing perfusion solution, and
  (4) obtaining an NMR measurement.

* * * * *